(12) United States Patent
Monti

(10) Patent No.: US 7,395,826 B2
(45) Date of Patent: Jul. 8, 2008

(54) MACHINE FOR WASHING AND/OR STERILIZING SUPPLYING-BATCHING DEVICES

(75) Inventor: Giuseppe Monti, Bologna (IT)

(73) Assignee: Tonazzi Vasquali S.r.L., Cerro Maggiore (Milano) (IT)

( * ) Notice: Subject to any disclaimer, the term of this patent is extended or adjusted under 35 U.S.C. 154(b) by 517 days.

(21) Appl. No.: 11/050,048

(22) Filed: Feb. 3, 2005

(65) Prior Publication Data

US 2005/0166948 A1 Aug. 4, 2005

(30) Foreign Application Priority Data

Feb. 3, 2004 (IT) .......................... BO2004A0044

(51) Int. Cl.
*B08B 3/00* (2006.01)
(52) U.S. Cl. ................... 134/94.1; 134/166 R; 134/177
(58) Field of Classification Search ................ 134/94.1, 134/166 R, 177
See application file for complete search history.

(56) References Cited

U.S. PATENT DOCUMENTS 3,693,640 A 9/1972 Wettlen et al.
5,295,523 A * 3/1994 Gentile ........................ 141/244
5,621,194 A * 4/1997 Koyama et al. .......... 177/25.18
6,161,558 A 12/2000 Franks et al.

FOREIGN PATENT DOCUMENTS

| DE | WO 02/060755 | 8/2002 |
|----|----|----|
| EP | 1170209 | 1/2002 |
| EP | 1170210 | 1/2002 |

\* cited by examiner

*Primary Examiner*—Alexander Markoff
*Assistant Examiner*—Jason Heckert
(74) *Attorney, Agent, or Firm*—William J. Sapone; Coleman Sudol Sapone P.C.

(57) ABSTRACT

In a machine for washing and/or sterilizing supplying-batching devices, an enclosing structure has supporting means for a supplying-batching device to be washed and/or sterilized. Feeding ducts are to be connected to a hopper of the supplying-batching device for feeding washing fluids. Working devices are to be connected to batching means and to supplying means of the supplying-batching device, and are to be operated to reproduce working operation of the batching means and supplying means, so as to perform working cycles with said washing fluids fed to the hopper.

9 Claims, 3 Drawing Sheets

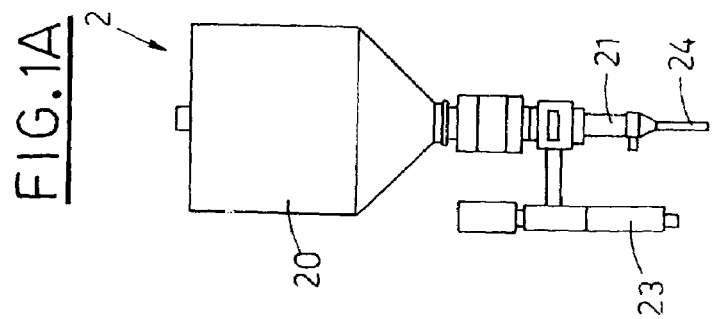
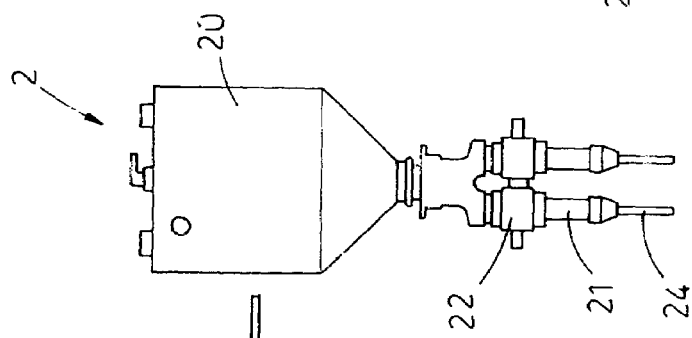
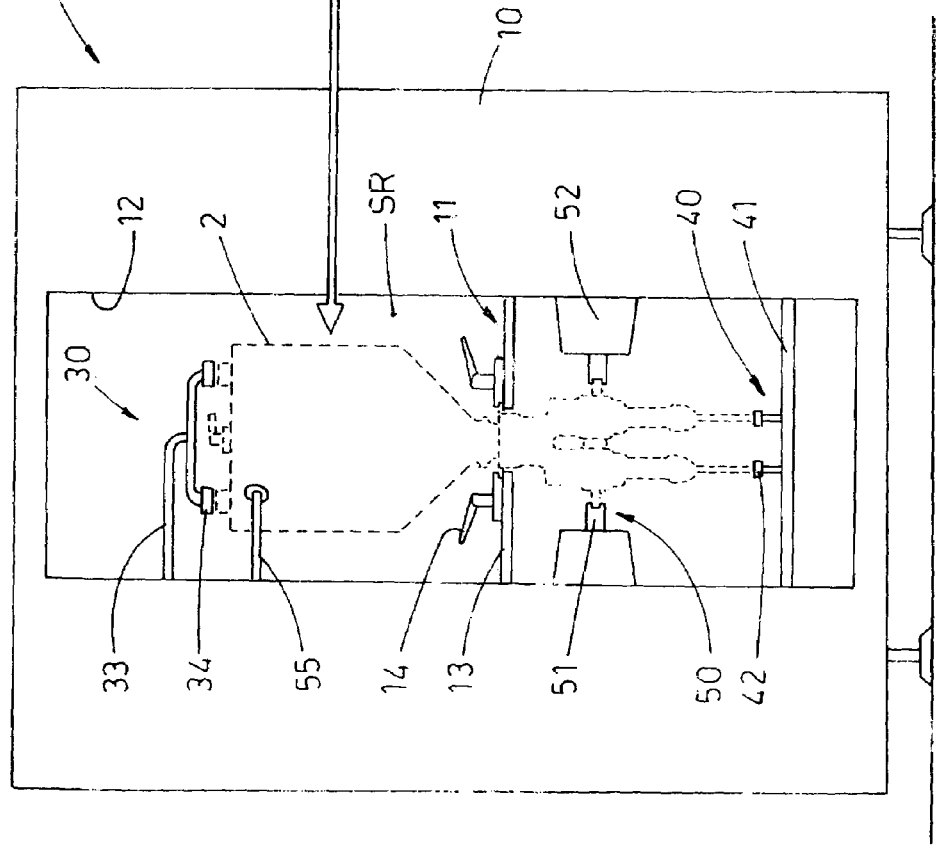

MACHINE FOR WASHING AND/OR STERILIZING SUPPLYING-BATCHING DEVICES

FIELD OF THE INVENTION

The present invention relates to filling of containers, in particular squeezable tubes, with paste products and the like. In particular, the invention relates to a machine for washing and/or sterilizing supplying-batching devices.

DESCRIPTION OF THE PRIOR ART

At present, there are apparatuses for automatic filling the squeezable tubes with batched quantities of paste products and subsequent closing the tubes.

These apparatuses generally include a feeding station, equipped with a device for supplying and batching the paste product.

An apparatus of this type is described in the document EP 1.170.210.

According to this known solution, the supplying-batching device includes substantially a hopper, which is fed with the product to be batched and from which the product is sent to batching means, for example, a syringe.

The syringe batching means communicate, via suitable valve means, with nozzle supply means for filling tubes, which are supplied with the opening turned upwards.

One of the problems occurring with the above apparatuses is connected with washing and/or sterilizing the supplying-batching device each time the product to supply is changed or in other similar circumstances.

At present, such operation includes, besides stopping the machine and removal of the whole supplying-batching device, disassembling of all working means making up the device.

Then, the disassembled working means are washed and/or sterilized, usually in an autoclave, and subsequently, assembled again, in order to reconstruct the supplying-batching device, which is mounted onto the apparatus for filling and closing tubes and the production resumes.

The washing and/or sterilization of the supplying-batching device is obviously difficult and requires relatively long time, as well as the necessary manpower, which increases the production costs.

SUMMARY OF THE INVENTION

The main object of the present invention is to resolve the above problem, by proposing a machine, which performs automatically the washing and/or sterilization of the supplying-batching devices, without dismantling the working means of the supplying-batching devices.

Another object of the present invention, resulting from the main one, is to propose a machine, whose constructive concept is simple, working reliable and use versatile.

The above mentioned objects are obtained in accordance with the contents of the claims, by a A machine for washing and/or sterilizing supplying-batching devices including a hopper, batching means and supplying means, the machine including:

a structure with a receiving station:

supporting means situated inside the structure for supporting a supplying-batching device to be washed and/or sterilized;

feeding means each time connected to said hopper of said supplying-batching device for feeding washing fluids thereto;

working means situated inside the structure and connected to said batching means and supplying means of said supplying-batching device, said working means being operated for reproducing working operation of said batching means and supplying means, so as to perform working cycles with said washing fluids fed to said hopper;

a plurality of channels for discharging said washing fluids, connected to supplying means of said supplying-batching device.

BRIEF DESCRIPTION OF THE DRAWINGS

The characteristic features of the invention will be pointed out in the following description of some preferred, non exclusive embodiments, with reference to the enclosed figures, in which:

FIG. 1 is a front schematic view of the proposed machine for washing and/or sterilizing a supplying-batching device, shown from outside;

FIG. 1A is a lateral view of the supplying-batching device, orthogonal to the one of FIG. 1;

DESCRIPTION OF THE PREFERRED EMBODIMENTS

Figure 2:
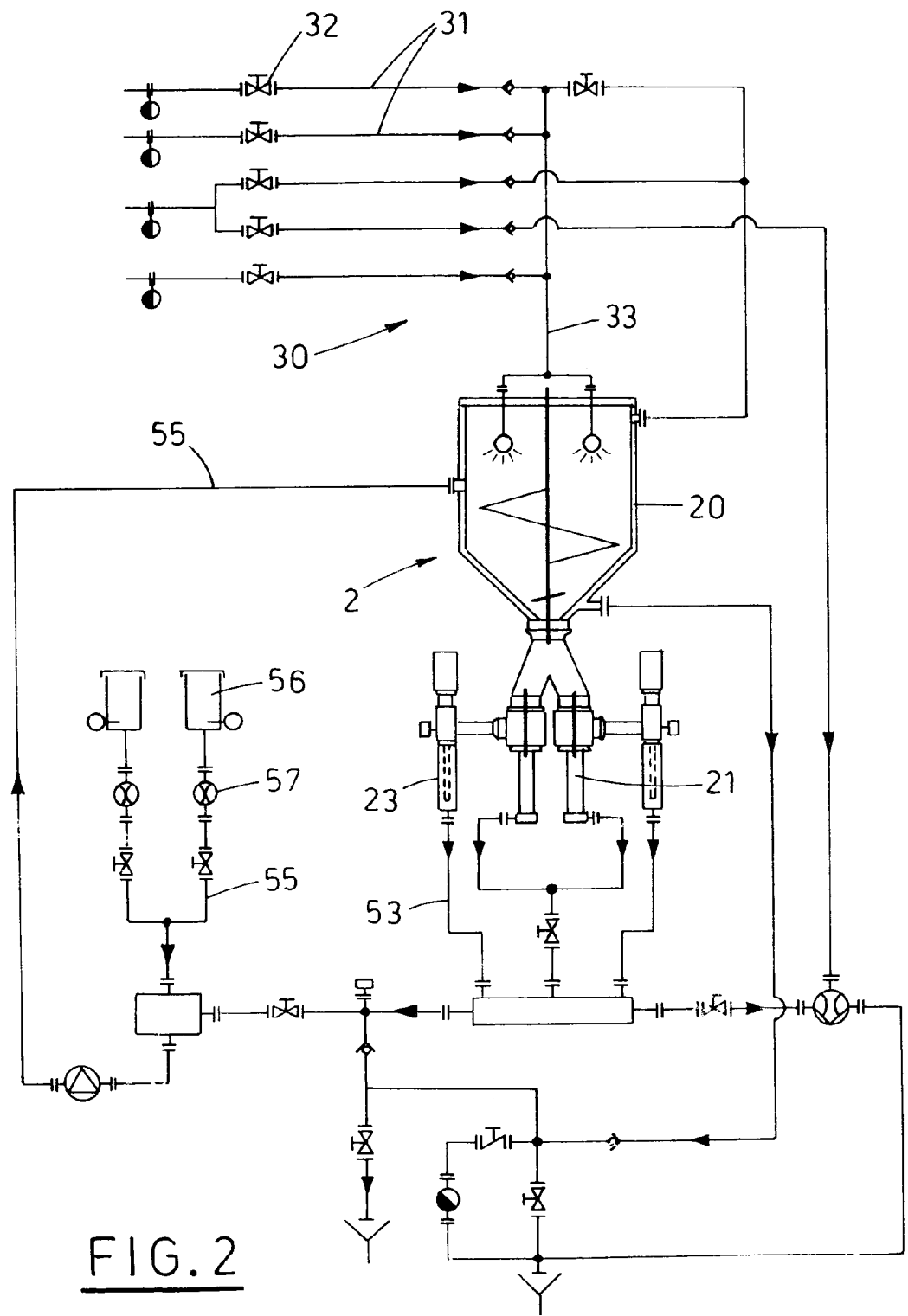
FIG. 2 is a circuit diagram of washing of the supplying-batching device.

With particular reference to the above Figures, the reference numeral 1 indicates the machine for washing and/or sterilizing of a supplying-batching device 2 aimed at being used with apparatuses of known type for filling containers, in particular squeezable tubes, with paste products and the like.

The supplying-batching device 2 includes substantially a hopper 20, which is fed, in normal operation conditions, with the paste product to be batched, and which is sent to the batching means 21, e.g. a syringe.

The syringe batching means 21 communicate, by suitable commutation valve means 22, with respective supplying nozzle means 23, which fill the tubes.

According to the shown example, the supplying-batching device 2 includes a pair of batching means 21 and supplying means 23 for filling contemporaneously two tubes.

The machine for washing and/or sterilizing the supplying-batching device 2 includes a structure 10, in which a receiving station SR is made for the supplying-batching device 2, practically reproducing the seat of the machine for filling and closing tubes, from which the supplying-batching device 2 has been dismantled.

The shape of the enclosing structure 10 is like a casing and the receiving station SR has an aperture 12, made in its front part, for the introduction of the supplying-batching device 2 to be washed and/or sterilized.

The aperture 12 is closed by a suitable door, made e.g. of transparent material to allow visual check of the operation steps.

The machine sterility can be increased, when required, by providing means (not shown) on the roof of the structure 10 for generating a laminar flow of air directed downwards into the receiving station SR, to sterilize the atmosphere in the station.

The receiving station SR includes supporting means 11 for the supplying-batching device 2 to be washed and/or sterilized, formed substantially by a plate 13, intermediate with respect to the structure 10 and having fastening means 14 for fixing stably the supplying-batching device 2 in the position indicated with the broken line in FIG. 1.

Feeding means 30 are situated inside the receiving station SR for being connected to the hopper 20 of the supplying-batching device 2, to deliver suitable washing fluids.

Working means 40, 50 are to be connected respectively to the syringe batching means 21 and to the valve means 22 of the supplying nozzle means 23.

As it will be specified in the following, the working means 40, 50 are operated by suitable motor means, to reproduce the usual working functions of the batching means 21 and supplying means 23, so as to perform a series of working cycles with the washing fluids fed to the hopper 20.

The feeding means 30 include a plurality of pipes 31, having respective interception valve means 32, for feeding different washing fluids, in particular water from the water system, sterile water, sterile air, steam.

The pipes 31 are set in communication with a feeding channel 33, which is to be connected to the top of the hopper 20, in correspondence to the traditional coupling means 34, made in the latter and normally used in the machine for filling and closing tubes to connect the inlet channels of the paste product to batch.

The first working means 40 include substantially a cross bar 41, situated horizontally in the lower part of the structure 10 and having connection means 42, which are to be connected with the pistons 24 of the syringe batching means 21.

The cross bar 41 is translated vertically by suitable motor means, so as to operate the above pistons 24.

Suitably, the cross bar 41 makes the pistons 24 of the syringe batching means 21 perform a path, whose extension is bigger with respect to the maximum stroke normally performed in the tubes filling machine.

The second working means 50 include substantially gripping means 51, which are fixed to the commutation valve means 22 of the supplying nozzle means 23.

The gripping means 51 are operated to rotate angularly by suitable activating means 52, preferably a respective rotating piston.

The gripping means 51 make the valve means 22 rotate by 90° during the washing step and by 180° during the sterilizing step.

The nozzles of the supplying means 23 are connected to respective channels 53 for discharging fluids used for washing.

The washing circuit includes also a channel 55 for supplying detergent substances, fed from small tanks 56 by suitable batching pumps 57.

Figure 3:
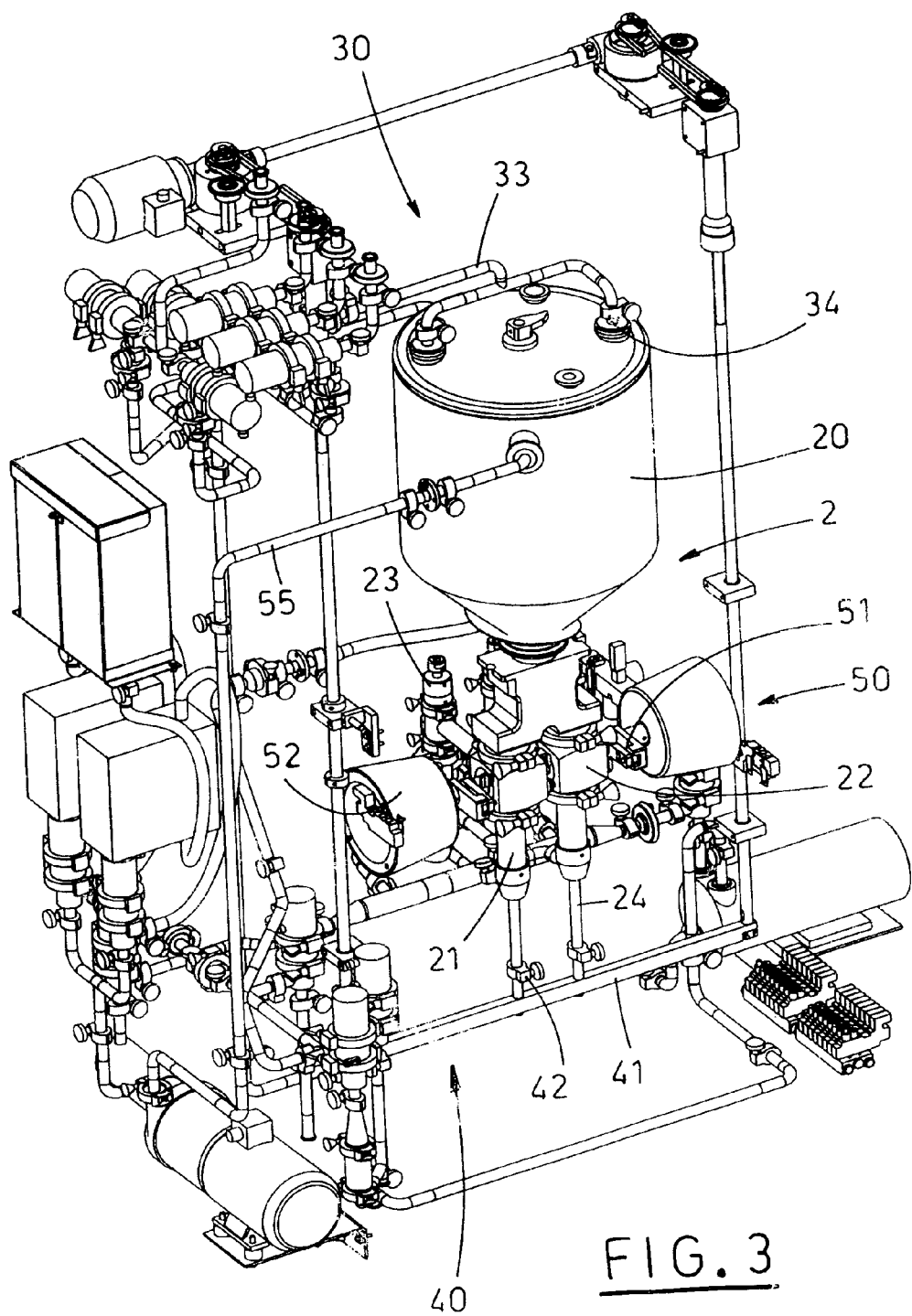
FIG. 3 is a prospective view of the washing circuit, with its working means.

The supply channel 55 leads to a side of the hopper 20 (see FIGS. 2 and 3).

The supplying-batching device 2, in order to be washed and/or sterilized, is first removed from the machine for filling and closing tubes, then mounted inside the machine 1, by fixing to the plate 13 of the support means 11.

The different working means of the supplying-batching device 2 are then connected, as it has been shown previously, to the corresponding feeding means 30 and the working means 40, 50 of the machine.

At this point, a series of working cycles can be performed with washing fluids fed to the hopper 20 of the supplying-batching device 2.

Obviously, these working cycles are different in function to the kind of paste product to be removed and to the kind of washing and/or sterilizing required in relation to this product.

It is to be noted that the washing and/or sterilizing of the supplying-batching device are performed inside a closed environment, defined by the structure 10 of the machine, made perfectly sterile according to the regulations.

Therefore, the proposed machine fulfills the object of automatic washing and/or sterilizing the supplying-batching devices without dismantling the working means of the supplying-batching devices, which results obviously in reduction of time and man labor.

This is obtained particularly due to the fact that the machine can reproduce substantially the working functions of different working means of the supplying-batching device, in particular the syringe batching means and the nozzle supply means.

In other words, the supplying-batching device inside the machine performs a series of working cycles, which simulate the normal operation performed by the above working means, making circulate the suitable washing and/or sterilizing fluids.

These operations can be suitably increased with respect to the normal working conditions, to ensure the reaching of the required washing and/or sterilizing degree.

In particular, the pistons 24 of the syringe batching means 21 are made perform a path, whose extension is greater than the maximum stroke normally performed in the tubes filling machine and the valve means 22 perform a 180° rotation during the sterilizing step, greater than the rotation performed normally.

One of the prerogatives of the proposed machine lies in the fact that the working cycles can be programmed in different ways, in relation to the characteristics of the products to remove.

In practice, the machine working can be regulated according to a wide range of working modes in relation to the users' specific needs.

Obviously, traditional electronic control means allow to perform automatically the above mentioned working cycles, according to a prefixed program.

The proposed machine is also safe to use for the operators, who introduce the supplying-batching device by a suitable carriage and thus they can control the execution of the working step from outside.

It is understood that the proposed invention has been described, with reference to the enclosed figures, as a mere, not limiting example. Therefore, it is obvious that any changes or variants applied thereto remain within the protective scope defined by the following claims.

What is claimed is:

1. A machine for washing and/or sterilizing a supplying-batching device having a hopper, piston batching means having movable pistons for delivering batched quantities of a product therefrom, and supplying means having a commutation valve and supplying nozzles for delivering product therethrough, said piston batching means communicating with said supplying nozzles through said commutation valve, the machine comprising:

an enclosing structure enclosing a receiving station having supporting means for supporting the supplying-batching device to be washed and/or sterilized;

fluid feeding means located within the enclosing structure and being connectable to said hopper of said supplying-batching device for feeding washing fluids thereto;

working means situated inside the enclosing casing structure which are connectable to said piston batching means and said supplying means of said supplying-batching device, said working means operating the supplying-batching device to reproduce a working cycle of said piston batching means and said supplying means, so as to perform one or more working cycles as said washing fluids are fed to said hopper, said working means including piston working means, connectable with the pistons for moving the pistons, and gripping means fixable to said commutation valve and operable for angularly rotating said commutation valve, and, a plurality of channels provided within the enclosing structure for receiving discharged washing fluids from the supplying of said supplying-batching device.

2. A machine, as claimed in claim 1, wherein said fluid feeding means include a plurality of pipes having respective intercepting valve means for supplying different washing fluids thereto, a feeding channel connected to a top of said hopper, the plurality of pipes communicating with the feeding channel which is located in a region corresponding to connecting means normally used on the hopper for introducing a product thereto.

3. A machine, as claimed in claim 1, wherein said piston working means include a cross bar, situated horizontal in a lower part of said enclosing structure and having coupling means fastenable to the pistons of said piston batching means, said cross bar being vertically translatable by motor means for operating the pistons.

4. A machine, as claimed in claim 1, further comprising activating means connected to said gripping means for activating the rotation of the gripping means so as to angularly rotate said commutation valve.

5. A machine, as claimed in claim 1, wherein said piston working means are operable to stroke the pistons of the piston batching means to an extent greater than a stroke performed by the pistons during a normal operating cycle, and said gripping means are operable for making the commutation valve perform an angular rotation greater than an angular rotation performed by the commutation valve during the normal operating cycle.

6. A machine, as claimed in claim 1, further comprising a washing circuit having a channel leading to a side of said hopper for delivering detergent substances thereto, delivered to said channel from a plurality of small tanks by batching pumps.

7. A machine, as claimed in claim 1, wherein said enclosing structure has an aperture made in a front part thereof for admitting said supplying-batching device into said enclosing structure, a door provided for covering said aperture.

8. A machine, as claimed in claim 1, wherein said enclosing structure has a box-like shape and has, in an upper part, means for generating a laminar flow, which is directed downward into said receiving station for sterilizing an atmosphere enclosed therein.

9. A machine for washing and/or sterilizing a supplying-batching device having a hopper, piston batching means having movable pistons for delivering batched quantities of a product therefrom, and supplying means having a commutation valve and supplying nozzles for delivering product therethrough, said piston batching means communicating with said supplying nozzles through said commutation valve, the machine comprising:

an enclosing structure enclosing a receiving station having supporting means for supporting the supplying-batching device to be washed and/or sterilized;

fluid feeding means located within the enclosing structure and being connectable to said hopper of said supplying-batching device for feeding washing fluids thereto;

working means situated inside the enclosing casing structure which are connectable to said piston batching means and said supplying means of said supplying-batching device, said working means operating the supplying-batching device to reproduce a working cycle of said piston batching means and said supplying means, so as to perform one or more working cycles as said washing fluids are fed to said hopper, said working means including piston working means comprising a cross bar, situated in a lower part of said enclosing structure and having coupling means which are fastenable to said pistons, said cross bar being translatable by motor means so as to displace the pistons during the washing and/or sterilizing of the supplying-batching device, and gripping means fixable to said commutation valve, activating means connected to the gripping means for angularly rotating said gripping means and said commutation valve during the washing and/or sterilizing of the supplying-batching device, and, a plurality of channels provided within the enclosing structure for receiving discharged washing fluids from the supplying means of said supplying-batching device.

\* \* \* \* \*